United States Patent
Roskamp et al.

(10) Patent No.: US 9,678,066 B2
(45) Date of Patent: Jun. 13, 2017

(54) METHOD AND KIT FOR MEASURING INTERACTION BETWEEN MOLECULES

(71) Applicant: PHARMADIAGNOSTICS NV, Zellik (BE)

(72) Inventors: Meike Roskamp, Papenburg (DE); Vanessa Bonnard, Uccle (BE); Sylviane Boucharens, Lanarkshire (GB)

(73) Assignee: PHARMADIAGNOSTICS NV, Zellik (BE)

( * ) Notice: Subject to any disclaimer, the term of this patent is extended or adjusted under 35 U.S.C. 154(b) by 162 days.

(21) Appl. No.: 14/376,503

(22) PCT Filed: Feb. 15, 2013

(86) PCT No.: PCT/EP2013/053103
§ 371 (c)(1),
(2) Date: Aug. 4, 2014

(87) PCT Pub. No.: WO2013/121011
PCT Pub. Date: Aug. 22, 2013

(65) Prior Publication Data
US 2015/0024402 A1  Jan. 22, 2015

Related U.S. Application Data (60) Provisional application No. 61/599,455, filed on Feb. 16, 2012.

(30) Foreign Application Priority Data

Feb. 16, 2012 (GB) .................................. 1202631.6

(51) Int. Cl.
*G01N 33/53* (2006.01)
*B82Y 15/00* (2011.01)
(Continued)

(52) U.S. Cl.
CPC .......... *G01N 33/5306* (2013.01); *B82Y 15/00* (2013.01); *B82Y 30/00* (2013.01);
(Continued)

(58) Field of Classification Search
None
See application file for complete search history.

(56) References Cited

U.S. PATENT DOCUMENTS

2006/0275310 A1  12/2006  Dwarakanath et al.
2008/0213814 A1  9/2008  Gerion et al.
(Continued)

FOREIGN PATENT DOCUMENTS

WO  WO 2010/029175 A1  3/2010
WO  WO 2011/104497 A1  9/2011

OTHER PUBLICATIONS

Li et al., LSPR Sensing of Molecular Biothiols Based on Noncoupled Gold Nanorods, Langmuir, 26 (11), pp. 9130-9135, published online Apr. 28, 2010.*

(Continued)

*Primary Examiner* — Rebecca Martinez
(74) *Attorney, Agent, or Firm* — Knobbe, Martens, Olson & Bear LLP (57) ABSTRACT

The present invention relates to methods of measuring interaction between a first and a second molecule, for example a protein and an antibody, by conjugation of one of these molecules with nanoparticles, and measuring the interaction between the first and second molecule via changes in the optical properties of the nanoparticles. The present invention further relates to methods of coating nanoparticles.

13 Claims, 4 Drawing Sheets

(51) Int. Cl.
    *B82Y 30/00*    (2011.01)
    *G01N 33/543*   (2006.01)
    *G01N 33/58*    (2006.01)
(52) U.S. Cl.
    CPC . *G01N 33/54306* (2013.01); *G01N 33/54313* (2013.01); *G01N 33/54353* (2013.01); *G01N 33/587* (2013.01)

(56) References Cited

U.S. PATENT DOCUMENTS

2009/0029391 A1   1/2009   Englebienne et al.
2009/0148863 A1   6/2009   Xu et al.

OTHER PUBLICATIONS

International Search Report and Written Opinion of the International Searching Authority for International Application No. PCT/EP2013/053103, mailed on Jun. 13, 2013.
Written Opinion of the International Preliminary Examining Authority for International Application No. PCT/EP2013/053103, mailed on Feb. 27, 2014.
International Preliminary Report on Patentability for International Application No. PCT/EP2013/053103, mailed on May 19, 2014.
Chen et al., "Atomic force bio-analytics of polymerization and aggregation of phycoerythrinconjugated immunoglobulin G molecules," *Molecular Immunology*, vol. 41, pp. 1247-1252 (2004).
Chen et al., "Ultrasensitive protein detection in blood serum using gold nanoparticle probes by single molecule spectroscopy," *Journal of Biomedical Optics*, vol. 14(4), pp. 040501-1-040501-3 (Jul./Aug. 2009).
Ravindranath et al., "Biofunctionalized Magnetic Nanoparticle Integrated Mid-Infrared Pathogen Sensor for Food Matrixes," *Anal. Chem.*, vol. 81, pp. 2840-2846 (2009).
Sun et al., "Surface-Enhanced Raman Scattering Based Nonfluorescent Probe for Multiplex DNA Detection," *Anal. Chem.*, vol. 79, pp. 3981-3988 (2007).
Yu et al., "Multiplex Biosensor Using Gold Nanorods," *Anal. Chem.*, vol. 79, pp. 572-579 (2007).
Wang et al., "Gold Nanorod Probes for the Detection of Multiple Pathogens," *Small*, vol. 4(12), pp. 2204-2208 (2008).
Search Report issued in United Kingdom Patent Application No. GB1202631.6, dated Jun. 14, 2012.
Further Search Report issued in United Kingdom Patent Application No. GB1202631.6, dated Dec. 17, 2012.
Grabinski et al., "Effect of Gold Nanorod Surface Chemistry on Cellular Response", *ACS NANO*, vol. 5(4), pp. 2870-2879 (Mar. 15, 2011).
Mayer et al., "A Label-Free Immunoassay Based Upon Localized Surface Plasmon Resonance of Gold Nanorods," *ACS NANO*, vol. 2(4), pp. 687-692 (Feb. 22, 2008).
Wijaya et al., "Ligand Customization and DNA Functionalisation of Gold Nanorods via Round-Trip Phase Transfer Ligand Exchange," *Langmuir*, vol. 24(18), pp. 9966-9969 (Aug. 22, 2008).

\* cited by examiner

METHOD AND KIT FOR MEASURING INTERACTION BETWEEN MOLECULES

CROSS-REFERENCE TO RELATED APPLICATIONS

This application is the U.S. National Phase under 35 U.S.C. §371 of International Application PCT/EP2013/053103, filed Feb. 15, 2013, which claims priority to GB 1202631.6, filed Feb. 16, 2012 and U.S. Provisional Application No. 61/599,455, filed Feb. 16, 2012.

FIELD OF THE INVENTION

The present invention relates to methods of measuring interaction between a first and a second molecule, for example a protein and an antibody, by conjugation of one of these molecules with nanoparticles, and measuring the interaction between the first and second molecule via changes in the optical properties of the nanoparticles. The present invention further relates to methods of coating nanoparticles.

BACKGROUND OF THE INVENTION

Metal nanoparticles coated with molecules such as proteins can be used to determine binding events by monitoring a change in optical properties of the particles, such as by Localized Surface Plasmon Resonance (LSPR) sensing. In the common scheme a recognition interface is constructed on the metal nanostructure. The specific binding of an analyte to said recognition interface is converted into an optical signal, e.g. a change in absorbance (wavelength, intensity) which is detected and analyzed.

LSPR sensing is based on the sensitivity of the localized plasmon absorbance of metal nanoparticles to changes in the dielectric properties of the contacting medium.

In principle LSPR can be used in the detection of antibody-ligand interactions, receptor-ligand interactions, enzyme-ligand binding and antibody-antigen association-dissociation kinetics.

In practice, however it is observed that such methods where nanoparticles are used in solution often do not attain the required accuracy.

Thus, there remains a need in the art to provide methods which allow the accurate determination of interactions between molecules using nanoparticles.

SUMMARY OF THE INVENTION

The present invention relates to methods of measuring interaction between a first and a second molecule by conjugation of one of these molecules with nanoparticles, and measuring the interaction between the first and second molecule via changes in the optical properties of the nanoparticles. The present invention allows using nanoparticles in quantities which are sufficient for reliable detection, while avoiding or at least reducing ligand depletion.

In a first aspect, the present invention provides a method of determining an interaction between a first and a second molecule comprising:
 a) providing nanoparticles comprising one or more metals;
 b) providing said nanoparticles with one or more functional groups, or coupling the first molecule to a molecule comprising a metal binding functionality;
 c) conjugating said first molecule to said nanoparticles, whereby the amount of said first molecule attached to said nanoparticles is less than 70%, and preferably between 10% and 70%, of the amount required for full coverage of said nanoparticles with said first molecule;
 d) incubating said nanoparticles with said second molecule;
 e) monitoring step d) by illuminating said nanoparticles with at least one excitation light source and monitoring one or more optical properties of said nanoparticles; and
 f) detecting a change of one or more optical properties of said nanoparticles wherein said change is a result of the presence of an interaction between said first molecule and said second molecule.

In particular embodiments, the nanoparticles comprise gold, silver or copper. In certain embodiments, the nanoparticles are nanorods.

In particular embodiments, step f) comprises determining an association-dissociation equilibrium between said first and second molecule. In certain embodiments, step f) comprises measuring said one or more optical properties at two or more wavelengths ranging between 350 and 1000 nm.

In particular embodiments, step b)) comprises providing nanoparticles having attached to their surface:
 one or more molecules comprising a metal binding functionality, and a functional group selected from carboxyl, amino, azido, alkynyl, carbonyl and hydroxyl; and
 one or more molecules comprising said metal binding functionality and not comprising said functional group selected from carboxyl, amino, azido, alkynyl, carbonyl and hydroxyl.

In certain embodiments, step c) comprises:
 c1) optionally, selecting a suitable pH and ionic strength for conjugation of said first molecule with said nanoparticles via a buffer test;
 c2) determining the amount of said first molecule needed for conjugation of said first molecule to said nanoparticles;
 c3) conjugation of said first molecule to said nanoparticles, based on the information obtained in step c2) and optionally c1).

In further embodiments, step c2) comprises a concentration titration of said nanoparticles with said first molecule, optionally at the pH and ionic strength selected in step c1).

In particular embodiments, step b) comprises coupling said first molecule to a linker molecule having a metal binding functionality and step c) comprises conjugation of said first molecule to said nanoparticle via said linker molecule. In further embodiments, the linker molecule is a mercaptocarboxylic acid.

In certain embodiments, the first molecule is a protein and the surface of said nanoparticles is provided with carboxyl groups. In further embodiments, the present method further comprises reacting free carboxyl groups on the surface of said nanoparticles with a carboxyl blocking compound.

In a further aspect, the present invention provides a method of coating a metal nanoparticle with a compound, comprising:
 i) providing a liquid composition comprising metal nanoparticles at least partially coated with cetyl trimethyl ammonium bromide (CTAB);
 ii) adding a thiol-polyethylene glycol to said composition, thereby obtaining a liquid composition comprising metal nanoparticles coated with thiol-polyethylene glycol;

iii) purification of said composition obtained in step ii) by separating said nanoparticles from free thiol-polyethylene glycol and free CTAB;

iv) adding a mercaptocarboxylic acid to said composition obtained in step thereby obtaining a liquid composition comprising metal nanoparticles coated with mercaptocarboxylic acid, and v) contacting said metal particles obtained in step iv) with said compound.

In certain embodiments, the liquid composition in steps i), ii), iii) and iv) is an aqueous composition.

In a further aspect, the present invention provides a kit comprising:

a medium comprising a plurality of metal nanoparticles;

instructions for use of said nanoparticles in the method of determining an interaction between a first and a second molecule according to the present invention;

optionally, said first molecule; and optionally, said second molecule.

BRIEF DESCRIPTION OF THE DRAWINGS

The invention will now be described, inter alia with reference to the accompanying Figures, which are provided by way of example only and should not be considered to limit the scope of the present invention.

DETAILED DESCRIPTION OF THE INVENTION

The present invention will be described with respect to particular embodiments but the invention is not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

As used herein, the term "localized surface plasmon resonance" or "LSPR" relates to methods which detect changes at or near the surface of metal nanoparticles. Typically, these changes are detected by detecting changes in one or more optical properties of the particles. When the metal surfaces of the nanoparticles are excited by electromagnetic radiation, they exhibit collective oscillations of their conduction electrons, known as localized surface plasmons (LSPs). When excited in this fashion, the nanoparticles act as nanoscale antennas, concentrating the electromagnetic field into very small volumes adjacent to the particles. Exceptionally large enhancements in electromagnetic intensity can be obtained this way. The nanoparticles used in the LSPR enable the occurrence of the resonance oscillations.

As used herein, the term "absorbance" refers to the extent to which a sample absorbs light or electromagnetic radiation in the UV, visual or near infrared range of the spectrum. In LSPR changes in refractive index may be detected through monitoring changes in the absorbance. Upon illumination of a sample, changes in the LSPR extinction band cause changes in the intensity and/or the wavelength of maximum absorbance.

The term "colloid" refers to a fluid composition of particles suspended in a liquid medium. In representative colloids, the particles therein are between one nanometer and one micrometer in size.

The term "sample" as used herein refers to a fluid composition, where in certain embodiments the fluid composition is an aqueous composition. While a skilled person would understand that any type of sample may be used in the context of the present invention, non-limiting examples include biological samples, including patient samples and environmental samples, plasma, hybridoma supernatants etc.

The term "$C_{4-16}$alkyl", as a group or part of a group, refers to a hydrocarbyl radical of Formula $C_nH_{2n+1}$ wherein n is a number ranging from 4 to 16. Alkyl groups may be linear, or branched and may be substituted as indicated herein.

When a subscript is used herein following a carbon atom, the subscript refers to the number of carbon atoms that the named group may contain. Thus, for example, $C_{6-12}$alkyl means an alkyl of 6 to 12 carbon atoms. Examples of alkyl groups are octyl, decyl, undecyl and its chain isomers.

The term "$C_{4-16}$alkylthiol" refers to HS—$R^w$, wherein $R^w$ is $C_{4-16}$ alkyl. Non-limiting examples of suitable $C_{4-16}$alkylthiol include undecane-1-thiol, decane-1-thiol or octane-1-thiol.

The term "azido" refers to —$N_3$. The term "amino" by itself or as part of another substituent, refers to —$NH_2$.

The term "alkynyl" refers to a branched or unbranched and cyclic or acyclic unsaturated hydrocarbon group comprising at least one triple bond. Non-limiting examples of alkyl groups include ethynyl, propynyl, 1-butynyl, 2-butynyl and the like.

The term "aqueous" as used herein means that more than 50 percent by volume of the solvent is water. Aqueous compositions or dispersions may further comprise organic liquids which are miscible with water.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the features of the claimed embodiments can be used in any combination.

The present invention relates to the use of nanoparticles for determining the interaction between a first and a second molecule, more particularly the provision of methods and tools to increase the accuracy of detection of such interactions. Indeed, the present inventors have found that the accuracy of detection is very much dependent on the coating of the nanoparticles.

In general, the binding of a ligand to a specific receptor or binding site may be characterized by the equilibrium dissociation constant ($K_d$). According to the law of mass action the $K_d$ of receptor or binding site ligand binding is dependent on both the association ($k_{on}$) and dissociation ($k_{off}$) rates and determined as the ratio of $k_{off}$ to $k_{on}$.

$$K_d = k_{off}/k_{on}$$

Standard methods of analyzing $K_d$ parameter (saturation binding) typically assume that the concentration of free ligand is constant during the experiment and the free ligand concentration does not significantly differ from the total added ligand concentration. In order to meet this constraint, the receptor or binding site concentration must be rather low, compared with the $K_d$ value. However, in some experimental situations, where the receptors or binding site are present in high concentration and have a high affinity for the ligand, that assumption is not true and the free ligand concentration is depleted by binding to the receptors or binding sites. This is known as "ligand depletion". Ligand depletion significantly impedes data analysis, and may lead to inappropriate values being derived for the binding parameters $k_{off}$, $k_{on}$ and $k_d$.

Therefore, when using bioconjugated metal nanoparticle suspensions for the determination of ligand-receptor interactions, and more particularly a $K_d$ and/or $k_{on}$ value, ligand depletion should be avoided. In practice, this means that less than 10% of the ligand in solution should bind to the receptors or binding sites. Although ligand depletion may already be reduced by reducing the concentration of nanoparticles comprising the receptor, a minimum amount of nanoparticles is required for reliable detection, the ratio of surface area to volume of nanomaterials is very high compared to bulk materials (for example SPR sensors or wells in a microplate) and enables the presentation of a large number of binding sites per nanoparticle. Therefore, reducing the nanoparticle concentration is often not sufficient to adequately reduce ligand depletion as the signal to noise ratio is decreasing too. The inventors have found a method for determining interactions between molecules without reducing the nanoparticle concentration, which maintains an acceptable signal to noise ratio value and decreases the effects of ligand depletion, thus enabling the determination of more accurate binding parameters.

Thus, in a first aspect, the present invention provides a method for studying potential interactions between a first molecule and a second molecule with improved accuracy, particularly in terms of derivation of correct binding parameters. The methods of the invention comprise the use of nanoparticles which are conjugated with the first molecule and then contacted with the second molecule, whereby the interaction between the first and the second molecule is determined by monitoring a change in optical properties. Most particularly, the methods comprise the use of nanoparticles, whereby the amount of the first molecule attached to the nanoparticles is less than 70% of the amount required for full coverage of said nanoparticles with the first molecule. Indeed, in the present methods, the amount of the first molecule attached to the nanoparticles can be controlled to be less than 70% of the amount required for full coverage. In particular embodiments, the methods according to the present invention comprise the steps of:

a) providing nanoparticles comprising one or more metals;
b) providing said nanoparticles with one or more functional groups, or coupling the first molecule to a linker molecule comprising a metal binding functionality;
c) conjugating said first molecule to said nanoparticles, wherein the amount of said first molecule attached to the nanoparticles is less than 70% of the amount required for full coverage of said nanoparticles with said first molecule;
d) incubating the nanoparticles with the second molecule;
e) monitoring step d) by illuminating said nanoparticles with at least one excitation light source and monitoring one or more optical properties of said nanoparticles; and
f) detecting a change of one or more optical properties of the nanoparticles wherein this change is a result of the presence of an interaction between the first molecule and the second molecule.

In particular embodiments, the first and second molecule are a member of a specific known or envisaged binding pair or couple. Thus, the second molecule (or potential cognate ligand) may refer to a molecule which potentially interacts with the first molecule. Typically the first molecule and second molecule are both sensing moieties which are members of a binding couple such as antigen-antibody, receptor-ligand, enzyme-ligand, sugar-lectin, receptor-receptor binding agent, and others. In these embodiments, the methods according to the present invention may serve for sensing the interaction between the two members of the binding pair. Sensing moieties of interest include, but are not limited to biomolecules, where the term "biomolecule" refers to any organic or biochemical molecule, group or species of interest, e.g., that can specifically bind to an analyte of interest. Exemplary biomolecules include, but are not limited to peptides, proteins, amino acids and nucleic acids, small organic and inorganic molecules, ligands, etc. In particular embodiments, the first molecule is a protein.

In particular embodiments, the interaction measured between the first and second molecule is referred to as "binding". The term "binding" refers to two molecules associating with each other in a non-covalent or covalent relationship.

The nanoparticles can be of any suitable shape and composition and can include but are not limited to nanorods, nanospheres, nanopyramids, nanowires, nanoprisms, nanocubes, nanotetrapods, etc. One of skill in the art will appreciate that other nanoparticles may also be useful in the present invention.

In particular embodiments, the nanoparticles are nanorods. In further embodiments, the nanorods have an aspect ratio (i.e. length divided by width) ranging between 1.1 and 10, more particularly between 1.5 and 5. In certain embodiments, the nanorods have a width or diameter between 2 and 20 nm, more particularly between 5 and 18 nm, for example about 15 nm. In particular embodiments, the nanorods have a length between 4 and 60 nm, more particularly between 40 and 50 nm, for example about 48 nm.

The nanoparticles comprise or are made of one or more metals. In certain embodiments, the nanoparticles used in the context of the present invention comprise one or more metals selected from Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au and/or Ac. In an embodiment, the nanoparticles comprise a metal selected from the group comprising Au, Ag, Cu, Ta, Pt, Pd, and Rh. In certain embodiments, said metal is selected from gold, silver and copper.

The nanoparticles provided in step a) of the methods according to the invention are typically provided as a colloid.

The solvents suitable for suspending the nanoparticles may depend on the nature of the nanoparticle surface. For example, the nanoparticles may be coated with a hydrophobic or hydrophilic coating. If the nanoparticles are provided with a hydrophobic coating, the solvent may comprise one or more solvents selected from toluene, hexane, heptane, pentane, cyclohexane, cyclopentane, chloroform, etc. If the nanoparticles are provided with a hydrophilic coating, the solvent may comprise one or more solvents selected from water, ethanol, butanol, isopropanol, acetone, etc. In certain embodiments, the particles are suspended in an aqueous medium.

In particular embodiments, the colloid comprises the nanoparticles in such a concentration that the colloid has an absorbance at $\lambda_{max}$ between 0.3 and 4, more particularly between 0.7 and 1.2, wherein $\lambda_{max}$ is the maximal absorbance of the nanoparticles between 350 and 1000 nm.

In the methods of the present invention, the metal nanoparticles are optionally provided with one or more functional groups (referred to as step (b) above), preferably selected from amino, azido, alkynyl, carboxyl, hydroxyl and carbonyl. The functional groups may be used for conjugating the first molecule to the nanoparticles (as provided in step c) above) of the present method, and will be discussed further below.

The nanoparticles used in the methods of the present invention are conjugated to a first molecule. It has been found that the conjugation density is critical to ensure the required accuracy for optical detection of the interaction between the first and the second molecule, more particularly in the determination of association/dissociation kinetics. The methods of the present invention thus involve controlling the binding density of the first molecule to the nanoparticles, by conjugating the first molecule to the nanoparticles such that the nanoparticles are not fully covered with the first molecule. Thus, in a next step (corresponding to step c) described above) of the methods of the present invention, the first molecule is conjugated to the nanoparticles (provided in step b)), whereby the amount of the first molecule conjugated to the nanoparticles is less than 70% of the amount required for full coverage of said nanoparticles with said first molecule. In particular embodiments, the amount of the first molecule conjugated to the nanoparticles is more than 10% of the amount required for full coverage. This allows using nanoparticles in quantities which are sufficient for reliable detection of interactions between the first and second molecule, while avoiding or at least reducing ligand depletion. In certain embodiments, the amount of the first molecule conjugated to the nanoparticles is more than 15% of the amount required for full coverage. In certain embodiments, the amount of the first molecule conjugated to the nanoparticles is more than 20% of the amount required for full coverage. The term "full coverage" as used herein refers to the maximal amount of the first molecule that can be conjugated or attached to a nanoparticle as a monolayer around said nanoparticle. Full coverage may be obtained by exposing the nanoparticles to a large excess of the first molecule in conditions suitable for coating the nanoparticles. In certain embodiments, the amount of the first molecule conjugated to the nanoparticles is less than 85, 80, 75, 70, 65, 60, 55, 50, 45, 40, 35, 30 or 25% of the amount required for full coverage. In particular embodiments, the amount of the first molecule conjugated to the nanoparticles is between 10% and 70%, preferably between 20% and 70%, more preferably between 20% and 60%, and even more preferably between 30 and 50% of the amount required for full coverage. The optimal amount of the first molecule may be determined via titration experiments and may depend on the characteristics of the nanoparticles, such as size and shape, and the first and/or second molecule. In particular embodiments, the amount of the first molecule conjugated to the nanoparticles is between 30 and 50%, preferably between 40 and 50%, of the amount required for full coverage, wherein the nanoparticles are nanorods with a length between 40 and 60 nm and a diameter between 10 and 20 nm.

The first molecule is typically adsorbed on/attached to/coupled to/linked to/bound to the surface of the nanoparticle, generally referred to herein as "conjugated to", by incubating the nanoparticles in a solution comprising the first molecule under conditions which allow the attachment of the first molecule onto the surface of the nanoparticles. Specifically, the first molecule may be conjugated to the nanoparticles by any one of a variety of methods, for example:

I) incubating nanoparticles which are provided with one or more functional groups with said first molecule, wherein said one or more functional groups are suitable to covalently bind the first molecule;

II) coupling the first molecule to a linker molecule which has a metal binding functionality, followed by conjugation of the first molecule to the nanoparticles via the linker molecule. Each of these methods can be used in a strategy to reduce the number of binding sites that are presented per nanoparticle.

Thus, in particular embodiments, the step of functionalizing the nanoparticles (corresponding to step b) described above) of the present method comprises providing the surface of nanoparticles (provided in step a)) with one or more functional groups suitable to covalently bind the first molecule. In particular embodiments, said functional groups are selected from carboxyl, amino, azido, alkynyl, carbonyl or hydroxyl.

Methods for functionalization of nanoparticles are well known to the skilled person, and may for example involve attachment of a linker molecule to the nanoparticle surface, wherein said linker molecule comprises a first portion linked to the nanoparticle (e.g. via a metal binding functionality) and a second portion which is a functional group capable of forming a covalent bond to the first molecule.

A variety of linker molecules is known to those of skill in the art and typically includes bifunctional molecules. Generally, such linker molecules will comprise a spacer group terminated at one end with a metal binding functionality and at the other end a functional group capable of covalently binding the first molecule.

Spacer groups of interest possibly include aliphatic and unsaturated hydrocarbon chains, spacers containing hetero-atoms such as oxygen (ethers such as polyethylene glycol) or nitrogen (polyamines), peptides, carbohydrates, cyclic or acyclic systems that may possibly contain hetero-atoms. The spacer group is preferably as short as possible, because it has been observed that the optical detection of the interaction of a biomolecule with a second molecule improves with reduced distance of the interaction to the nanoparticle surface. However, a spacer group which is too short may be insufficient to stabilize the nanoparticles in suspension. For optimal results, the spacer group preferably comprises a hydrocarbon chain with 6 to 18 and preferably 6 to 16 carbon atoms, for example 11 carbon atoms.

Potential functional groups capable of covalently binding the first molecule include nucleophilic functional groups (amines, alcohols, thiols, azides, hydrazides), electrophilic functional groups (alkynes, carboxyl, aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides.

Specific linker molecules that may find use in the subject bifunctional molecules include compounds such as mercaptocarboxylic acids such as 11-mercaptoundecanoic acid, 11-[2-(2-azido-ethoxy)-ethoxy]-undecane-1-thiol, azido-benzoyl hydrazide, N-[4-(p-azidosalicylamino)butyl]-3-[2'-pyridyldithio]propionamid), bis-sulfosuccinimidyl suberate, dimethyladipimidate, disuccinimidyltartrate, INI-maleimidobutyryloxysuccinimide ester, N-hydroxy sulfosuccinimidyl-4-azidobenzoate, N-succinimidyl[4-azidophenyl]-1,3'-dithiopropionate, N-succinimidyl[4-iodoacetyl] aminobenzoate, glutaraldehyde, and succinimidyl 4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

In particular embodiments, the one or more functional groups provided on the nanoparticle surface comprise carboxyl groups. Carboxyl groups are especially useful for binding proteins, because an activated carboxyl group can react with an amine moiety of a protein, thereby forming an amide bond. Accordingly, in particular embodiments, the nanoparticles are coated with one or more (linker) molecules comprising a carboxyl group and a metal binding functionality. In certain embodiments, the metal binding functionality is a sulfhydryl. Sulfhydryl moieties strongly bind to metal surface, particularly to gold surfaces. In further embodiments, the nanoparticles are at least partially coated with a mercaptocarboxylic acid. The sulfhydryl moiety of the mercaptocarboxylic acid can form a (coordination) bond with a metal atom of the nanoparticle surface, while the carboxyl moiety can be used to bind to molecules such as proteins. In particular embodiments, the mercaptocarboxylic acid is a molecule of formula (I):

wherein n is an integer from 6 to 16. In particular embodiments the mercaptocarboxylic acid is 11-mercaptoundecanoic acid.

In particular embodiments, one or more functional groups provided on the nanoparticles allow a coupling mechanism as used in Click Chemistry. For example, the functional groups may comprise an azide or an alkyne, thereby allowing an azide alkyne Huisgen cycloaddition using a Cu catalyst at room temperature, as known by the person skilled in the art. Accordingly, in particular embodiments, the nanoparticles are at least partially coated with a (linker) molecule of formula (IIa), (IIb), (IIIa) and/or (IIIb):

wherein na, nb, ng and ni are independently an integer from 6 to 16 and nh and nj are independently an integer from 1 to 5.

An azide functional group further provides the possibility of Staudinger ligation. Staudinger ligation typically involves reaction between an azide moiety with a phosphine or phosphate moiety. Accordingly, in certain embodiments, the nanoparticles are at least partially coated with a molecule of formula (IIa) or (IIb) as described above, wherein na and ng are independently an integer from 6 to 16.

In particular embodiments, the first molecule may as such not comprise a functional group suitable for covalently binding the functional groups provided on the nanoparticles. The methods according to the present invention may therefore comprise a further step of providing at least one functional group to the first molecule, prior to conjugation of the first molecule to the nanoparticles.

If the first molecule is conjugated to the nanoparticles via the functional groups as described above, the amount of functional groups provided on the nanoparticle surface determines the maximal amount of the first molecule that can be conjugated to the nanoparticles. Thus, by limiting the amount of functional groups, it can be ensured that less than full coverage of the nanoparticles by the first molecule is obtained, as required in the methods of the present invention. In particular embodiments this is ensured by contacting the nanoparticle with different linker molecules, one carrying the reactive functional group, the other not carrying the reactive functional group, such that the nanoparticle is coated with a mixture of reactive and non-reactive linkers. Thus, in particular embodiments, the nanoparticles used in the methods of the present invention are generated such that they comprise one or more linker molecules comprising a functional group and a metal binding functionality; and
one or more molecules comprising said metal binding functionality and not comprising said functional group. These one or more molecules are herein also referred to as "non-linker molecules".

The metal binding functionality ensures that the linker and non-linker molecules can be attached to the metal nanoparticle surface, while the functional group of the linker ensure that the first molecule can be covalently bound to the nanoparticles. As the non-linker molecules do not comprise the functional group, attachment of a sufficient amount of these molecules to the nanoparticle surface ensures that the amount of proteins conjugated to the nanoparticles is less than 70% of the amount required for full coverage of said nanoparticles with that protein.

Such a coating may be obtained by exposing the nanoparticles with a mixture of the linker and non-linker molecules. Alternatively, the coating may be obtained by fully or almost fully coating the nanoparticles with linker molecules, and partially exchanging the coating with non-linker molecules, or vice versa. Thus, the selection of the linker comprising non-functional groups is ideally selected such that a) it can be partially exchanged with a linker with a reactive functional group and b) it does not interfere with later reactions.

Examples of suitable linker molecules are described above. The one or more non-linker molecules are preferably structurally similar to the linker molecule. In certain embodiments, the non-linker molecules are identical to the linker molecule, except in that they lack the functional group. This typically results in a similar affinity and exchange characteristics of the linker and non-linker molecules to the nanoparticle surface. In certain embodiments, the non-linker molecules have a reduced length compared to the linker molecule. This reduces steric hindrance by the non-linker molecules upon reaction of the functional group of the linker molecules with the first molecule. However, in particular embodiments, the non-linker molecule(s) has/have a length similar to or greater than the linker molecule. This can further by the stability of the coating.

In particular embodiments, the non-linker molecule(s) comprise one or more functional groups which improve other characteristics of the nanomaterial such as solubility and/or stability. In particular embodiments, the presence of the non-linker molecules improves the stability of the nanoparticle suspensions. For example, if the non-linker molecules comprise sulfate, hydroxyl or polyethyleneglycol (PEG) moieties, the stability of the nanoparticle colloids in aqueous media can be improved.

In certain embodiments, the functional group of the linker molecule(s) is selected from carboxyl, azido, alkynyl, amino, carbonyl and hydroxyl. In certain embodiments, the functional group is selected from carboxyl, azido and alkynyl. In particular embodiments, the functional group is a carboxyl. In certain embodiments, said metal binding functionality is a sulfhydryl. In certain embodiments, the one or more linker molecules comprise a mercaptocarboxylic acid of formula (I) above such as 11-mercaptoundecanoic acid, and the one or more non-linker molecule is a compound of formula (IV) and/or (V):

wherein $R^1$ and $R^2$ are independently selected from sulfate, hydroxyl, hydrogen or methoxy;
wherein nc is such that the molecular weight of compound (IV) is between 100 Da and 10 kDa, more particularly between 100 Da and 1 kDa; and
nd is an integer from 6 to 16.

In specific embodiments, nc is an integer from 1 to 10. Typically, for the mixed monolayers the linker molecule is chosen to be relatively shorter, but provided the linker is sufficiently flexible (e.g. PEG), longer linkers can be used.

Less than full coverage may also be obtained by only letting a certain fraction of the functional groups provided on the nanoparticle surface react with the first molecule. The required amount of the first molecule to reach the desired coverage may be found by a titration experiment (see further). However, the unreacted functional groups still present on the nanoparticle surface area may cause nonspecific binding and a reduced stability of the nanoparticle conjugate, for example during purification and towards buffers. Accordingly, in particular embodiments, the non-reacted functional groups present on the nanoparticles are reacted with (an excess of) a blocking reagent after conjugation of the nanoparticles with the first molecule. The blocking reagent reacts with the remaining unreacted functional groups present on the nanoparticles, thereby preventing nonspecific binding.

Alternatively, less than full coverage may also be obtained by blocking a certain fraction of the functional groups provided on the nanoparticles with a blocking reagent, followed by reacting the non-blocked functional groups with (an excess of) the first molecule. To determine the optimal amount of blocking reagent required for blocking a certain part of the functional groups provided on the nanoparticles, a concentration titration may be performed.

The blocking reagent is typically chosen such that it does not significantly interact with the substances that shall be tested with the conjugated nanomaterial. In particular embodiments, the blocking reagent is further chosen such that it contributes to a good solubility of the conjugated nanoparticles in one or more solvents, for example by adding charge, hydrophilicity or sterical hindrance. Solubility of the conjugated nanoparticles in polar solvents may be increased by providing blocking reagents comprising one or more ethylene glycol moieties, and/or providing blocking reagents comprising one or more polar functional groups such as a sulfate, hydroxyl or methoxy.

If the functional group is a carboxyl, then the blocking reagent is a carboxyl blocking reagent. The carboxyl blocking reagent may comprise an amine group so as to react with the remaining activated carboxyl groups. In particular embodiments, the (carboxyl) blocking reagent is a compound of formula (VI) or (VII)

wherein $R^3$ and $R^4$ are independently selected from sulfate, hydroxyl, hydrogen and methoxy;
ne is such that the molecular weight of compound (VI) is between 89 Da and 10 kDa, preferably between 1 kDa and 10 kDa, for example 1 kDa; and
nf is such that the molecular weight of compound (IV) is between 30 Da and 500 Da. In particular embodiments, nf is an integer from 1 to 16, more particularly from 1 to 8.

As described above, the choice of blocking reagent may depend on various factors such as the substances that shall be tested with the protein conjugated nanomaterial. In particular embodiments, the carboxyl blocking reagent is selected from Bovine Serum Albumin (BSA), Ovalbumin, and an amino polyethylene glycol of formula (VI) as described above. These blocking reagents are particularly useful if the first molecule is Human Serum Albumin (HSA). In certain embodiments, any functional groups provided on the nanoparticles may be activated prior to reaction with the first molecule. If the functional group is a carboxyl, the carboxyl may be activated using one or more carboxyl activating groups. Useful carboxyl activating groups include, but are not limited to, carbodiimide reagents. In particular embodiments, activation of the carboxyl groups comprises addition of a N-hydroxysuccinimide (NHS) such as sulfo-NHS together with a coupling reagent such as ethyl(dimethylaminopropyl)car carbodiimide (EDC) or dicyclohexylcarbodiimide (DCC), preferably EDC. In certain embodiments, activation of the carboxyl groups comprises addition of sulfo-NHS together with EDC. This is herein also referred to as "sulfo-NHS/EDC coupling".

Alternative carboxyl activating groups include phosphonium reagents such as benzotriazolyloxy-tris-(dimethylamino) phosphonium hexafluorophosphate (BOP) and the like, uronium or carbonium reagents such as O-(benzotriazol-1-yl)-N,N,N',N'-tetramethyluronium hexafluorophosphate (HBTU), N-hydroxy-succinimide (NHS), benzotriazol-1-yl-oxy-tripyrrolidinophosphonium hexafluorophosphate (PyBOP) and the like; I-ethoxycarbonyl-2-ethoxy-I,2-dihydroquinoline (EEDQ); I-methyl-2-chloropyridinium iodide (Muikaiyama's reagent) and the like.

If the functional group is an azide, potential blocking reagents are molecules comprising a phosphine or alkyne moiety. If the functional group is an alkyne or phosphine, potential blocking reagents are molecules comprising an azide moiety. Examples of such molecules are modified proteins which do not significantly interact with the second molecule.

An alternative method for coupling the first molecule to the nanoparticles is by coupling the first molecule to a linker molecule which has a metal binding functionality in step b), followed by conjugation of the first molecule to the nanoparticles via the linker molecule in step c) (method II referred to above). The use of a linker with a metal binding functionality eliminates the need to provide the nanoparticles with functional groups for binding the first molecule. The first molecule is then conjugated to the nanoparticles via the linker molecule, more particularly via the metal binding functionality of the linker molecule. This is obtained by incubating the nanoparticles with (an excess of) the first molecule with the linker molecule attached thereto. In particular embodiments, the linker molecule comprises a carboxyl group and a metal binding functionality. The carboxyl group allows binding of the linker molecule to amine functions present on proteins. In certain embodiments, the linker molecule is a mercaptocarboxylic acid, for example mercaptoundecanoic acid.

In certain embodiments, the metal nanoparticles, e.g. gold nanoparticles, are coated with a thiol-PEG of formula (IV) as described above, prior to incubation with (an excess of) the first molecule with the linker molecule attached thereto. The thiol-PEG molecules are then at least partially exchanged for the first molecule, via the linker molecule. In particular embodiments, the use of nanoparticles coated with neutral thiol-PEG molecules such as methoxyl-PEG-thiol is particularly useful to prevent nanoparticle agglutination during conjugation with the first molecule. Indeed, for some proteins which are highly positively charged at pH 6-8, the use of the EDC/Sulfo-NHS coupling method on carboxyl-functionalized nanomaterials which are negatively charged can be challenging due to agglutination of the nanoparticles.

In particular embodiments, the step of conjugating said first molecule to said nanoparticles, includes the step of determining the amount of the first molecule required for obtaining the desired coverage of the nanoparticles. In further embodiments, step c) of the present method comprises:

c1) optionally, selecting a suitable pH and ionic strength for conjugation of said first molecule with said nanoparticles via a buffer test;
c2) determining the amount of said first molecule needed for conjugation of said first molecule to said nanoparticles;
c3) conjugation of said first molecule to said nanoparticles, based on the information obtained in step c2) and optionally c1).

Step c2) is typically performed by a concentration titration, wherein the nanoparticles are mixed with different amounts of protein and analyzed. The titration may be performed at the pH and ionic strength selected in step c1). The titration may be monitored via the measurement of the absorbance of the nanoparticles, preferably at two or more wavelengths.

In particular embodiments, step c2) comprises addition of different amounts of the first molecule to a fixed amount of nanoparticles and recording of absorbance spectra. Then, the ratio OD($\lambda$max+80)/OD($\lambda$max) ($\Delta$RU) may be plotted versus the amount of first molecule added. The conjugation of the first molecule to the nanoparticles leads to a difference in refractive index around the nanoparticles and thereby to a redshift of the $\lambda$max that can be detected by reading an absorbance spectrum. With increasing amount of the first molecule conjugated to the nanoparticles, the redshift also increases. After reaching the maximum amount of first molecule that can be conjugated to the nanoparticles the spectrum doesn't change anymore resulting in a plateau in the plot of OD(λmax+80)/OD(λmax) (ΔRU) versus the amount of first molecule. The lowest amount of protein on the plateau is the minimum amount of first molecule needed to fully cover the nanoparticle surface with the first molecule (or at least the LSPR sensitive part of the nanomaterial). In order to obtain a lower number of binding sites than what corresponds to full coverage of the nanoparticles with the first molecule, a lower amount of first molecule than the maximal amount can be used for conjugation. The optimal amount of first molecule to use for conjugation is a compromise between two tendencies, to ensure optimal sensitivity. Usually the ideal amount of protein to use is the amount that corresponds to 30-60% of the plateau.

If the nanoparticles are provided as a colloid, the colloid is preferably purified after conjugation of the first molecule to the nanoparticles, particularly when the conjugation of the first molecule to the nanoparticles occurs by incubating the nanoparticles in a solution comprising an excess of the first molecule. The excess of first molecules which are not bound onto the nanoparticles are preferably removed after conjugation. This may be obtained by one or more cycles of precipitation and resuspension of the nanoparticles as known by the skilled person.

After having obtained the nanoparticles suitably coated with the first molecule, in a next step (step d) of the present methods, the nanoparticles are incubated with the second molecule. Typically, the second molecule is provided in a (relatively) purified form in a fluid composition, which may be an aqueous composition and/or a buffer. In particular embodiments, the second molecule may be present in a biological sample.

Incubation of the nanoparticles with the second molecule allows interaction of the second molecule with the first molecule, which is conjugated to the nanoparticles. The proximity of the second molecule to the nanoparticles changes the dielectric medium surrounding the nanoparticles, which typically leads to changes of certain optical properties of the nanoparticle, such as the absorbance. Measuring one or more of these properties can therefore provide information of the interactions between the first and second molecule.

Accordingly, a further step (step (e) referred to above) of the presently claimed methods comprises monitoring the interaction between the first and second molecule as they are contacted (in step d) by illuminating the nanoparticles with at least one excitation light source and monitoring one or more optical properties of said nanoparticles. The light source typically emits light or radiation at one or more wavelengths between 220 and 1000 nm. In particular embodiments an excitation light source is used which emits light or radiation comprising between approximately 1 nanowatt and 100 watts of power. In more particular embodiments the excitation light source is a (xenon) flash lamp or a laser.

The monitoring of the optical parameters is used to detect a change therein, e.g., a change in absorption at a given wavelength. Any convenient optical parameter may be assessed or monitored in this step, where representative parameters include, but are not limited to: absorbance, refractive index, absorption, scattering, fluorescence, luminescence and the like. The optical parameter may be monitored using any convenient device and protocol, where suitable protocols are well known to those in the art. The presence or absence of a change in the optical parameter is then used to make a determination of whether or not the first molecule interacts with a second molecule, which in particular embodiments is used to provide an indication of the presence of an analyte of interest (second molecule) in a sample.

Accordingly, in a further step (step (f) referred to above) of the methods of the present invention, a change of one or more optical properties of said nanoparticles is detected. This change is a result of the presence of an interaction between the first molecule and the second molecule. Indeed, where the first and the second molecule interact, this will be detected as the optical properties of the nanoparticle will change. Where there is no interaction between the first and the second molecule, no change in optical properties will be detected.

The methods described herein comprise the step of detecting a signal, more particularly a change in signal at one or more wavelengths. The terms "monitoring", "determining", "measuring", "assessing", "detecting" and "evaluating" are used interchangeably to refer to any form of measurement, and includes not detecting any change. Said measurement may include both quantitative and qualitative determinations either relative or absolute and also include determining the amount of something present, as well as determining whether it is present or absent.

Thus, as used herein, the term "detecting" means to ascertain a signal (or a change therein), either qualitatively or quantitatively.

In particular embodiments, the one or more optical properties of the nanoparticles are measured at two or more wavelengths between 220 and 1000 nm, preferably between 350 and 1000 nm. Measurement at two or more wavelengths allows obtaining more accurate data. In particular embodiments, these wavelengths are discrete wavelengths within that range.

The methods of the present invention typically further comprise the step of analyzing the detected signal or change in signal and determining a particular property of the first or second molecule or of their interaction, based thereon.

In particular embodiments, the step of determining a change of one or more optical properties of said nanoparticles comprises determining the dissociation constant ($K_d$) or binding or association constant ($K_a$) for the association-dissociation equilibrium between the first and second molecule. The association-dissociation equilibrium can be represented by equation 1:

$$M1+M2 \leftrightharpoons M1M2 \qquad \text{(equation 1)}$$

wherein M1M2 represents an association or complex of M1 and M2.

The reaction is characterized by the on-rate constant $k_{on}$ and the off-rate constant $k_{off}$. In equilibrium, the forward binding transition M1+M2→M1M2 are balanced by the backward unbinding transition M1M2→M1+M2. Assuming a first-order reaction, that is, $$k_{on}[M1][M2]=k_{off}[M1M2] \qquad \text{(equation 2)}$$

where [M1], [M2] and [RL] represent the concentration of unbound free M1, the concentration of unbound free M2 and the concentration of M1M2 complexes, respectively. The association constant $K_a$ and dissociation constant $K_d$ are defined by:

$$K_a=1/K_d=k_{on}/k_{off}=[M1M2]/([M1][M2]) \qquad \text{(equation 3)}$$

Accordingly, if the concentrations of M1, M2 and M1M2 at equilibrium are known, $K_a$ and $K_d$ can be calculated. Alternatively, $K_a$ and $K_d$ may be calculated from a binding isotherm (see further).

From the association or dissociation constant, more information such as the association energy may be obtained.

In a further aspect, the present invention provides the use of the present method of determining an interaction between a first and a second molecule for preparing binding isotherms for binding of said second molecule to said first molecule, thereby assessing the binding affinity, binding constant $K_a$ or dissociation constant $K_d$ of said second molecule for said first molecule from said binding isotherm.

A binding isotherm may be constructed from the detected changes in the optical properties such as the refractive index or absorbance and the amount (or concentration) of second molecule added to the nanoparticles.

The methods of the present invention are also of interest in the context of screening methods. Thus in particular embodiments the present invention provides screening methods wherein detection is performed according to the present invention. In further embodiments, the methods are high-throughput screening methods, more particularly methods which are at least in part carried out in a high-throughput screening device.

The term "screening" refers to determining the presence of something of interest, e.g., an analyte, an occurrence, etc. As such the methods according to the present invention may be used to screen a sample for the presence or absence of one or more target analytes in the sample. As such, the invention provides methods of detecting the presence of one or more target analytes in a sample. In addition, the subject methods may also be used to screen for compounds that modulate the interaction of a given specific binding member pair. The term modulating includes both decreasing (e.g. inhibiting) and enhancing the interaction between the two molecules. For example, where the colloid displays a first member of a binding pair and the colloid is contacted with the second member in the presence of a candidate agent, the effect of the candidate agent on the interaction of the binding member pairs can be evaluated or assessed.

In yet a further aspect the present invention relates to tools for carrying out the methods of the present invention. More particularly, the tools include nanoparticles to which a first molecule has been conjugated. More particularly, the nanoparticles are conjugated such that there is not full coverage of the nanoparticles with the first molecule. In particular embodiments, the coverage is less than 70%, less than 60%, particularly between 30 and 50%.

The nanoparticles of the present invention can be obtained as described above by conjugating them with less than 70% of the amount required for full coverage of the nanoparticles with the first molecule.

The invention further provides kits for carrying out the methods of the present invention. More particularly the kits for carrying out the methods of the present invention comprise
a medium comprising a plurality of metal nanoparticles;
instructions for use of said nanoparticles in the methods according to the present invention;
optionally, said first molecule; and
optionally, said second molecule.

In particular embodiments, said nanoparticles are provided with functional groups, preferably selected from carboxyl, amino, azido, carbonyl and hydroxyl.

The kits of the present invention optionally also include solvents, buffers and/or stabilizers. The kits optionally also include one or more linker and/or non-linker molecules as described herein.

In particular embodiments, the nanoparticles are gold nanorods. Many methods for manufacturing gold nanorods are known to the skilled person. Typically, these methods involve the use of gold nanoparticle seeds and cetyl trimethyl ammonium bromide (CTAB) as a coordinating molecule, and result in nanoparticles which are fully coated with CTAB. However, in the methods of the present invention, particles fully coated with CTAB may not be suitable for conjugation to the first molecule. Therefore, an exchange of the CTAB coating to a coating of different molecules, such as mercaptocarboxylic acids, may be required. However, such an exchange typically requires long reaction times and/or various phase transfers between polar and non-polar phase. The inventors have found optimized coating methods which are particularly suitable for obtaining nanoparticles conjugated with a first molecule. These methods are of general interest for coating nanoparticles but can also be used in the methods of the present invention. Thus, in a further aspect, the present invention provides methods of coating a metal nanoparticle, comprising using metal nanoparticles with a CTAB coating to obtain nanoparticles with a mercaptocarboxylic acid coating. In particular embodiments, the methods of the invention comprise the steps of:
i) providing a liquid composition comprising metal nanoparticles at least partially coated with CTAB. Typically, the metal nanoparticles provided in this step are fully coated with one or more molecules, wherein the coating comprises CTAB. The coating may further comprise other molecules, such as benzyldimethylammoniumchloride.
ii) Adding a thiol-polyethylene glycol to said composition, thereby obtaining a liquid composition comprising metal nanoparticles coated with a thiol-polyethylene glycol.
iii) Purification of said composition obtained in step ii) by separating said nanoparticles from free thiol-polyethylene glycol and free CTAB.
iv) Adding a mercaptocarboxylic acid to said composition obtained in step iii, thereby obtaining a liquid composition comprising metal nanoparticles coated with a mercaptocarboxylic acid.

In contrast with known methods which require hydrophobic solvents in some steps, all steps of the method of coating a metal nanoparticle according to the present invention may be performed in aqueous phase. This significantly reduces potential health and safety issues and facilitates scaling up the nanoparticle production. Furthermore, this also results in reduced costs related to chemicals and waste management. Accordingly, in particular embodiments, the liquid composition in steps i), ii), iii) and iv) is an aqueous composition.

In particular embodiments, the mercaptocarboxylic added in step iv) is a compound of formula (I) described above.

In particular embodiments, the thiol-polyethylene glycol added in step ii) is a compound of formula (IV) as described above, wherein nc is such that the molecular weight of compound (IV) is between 100 Da and 10 kDa, preferably between 1 kDa and 10 kDa, for example 5 kDa; and $R^1$ is $C_{1-4}$alkoxy, preferably methoxy or ethoxy, wherein said $C_{1-4}$alkyl is optionally substituted by one or more groups such as hydroxyl.

The mercaptocarboxyl acid-coated nanoparticles obtained in step iv) as described above can be used to conjugate a molecule thereto. Accordingly, the present invention further provides a method for conjugating a molecule to a metal nanoparticle, comprising:
  i) providing a liquid composition comprising metal nanoparticles at least partially coated with CTAB;
  ii) adding a thiol-polyethylene glycol to said composition, thereby obtaining a liquid composition comprising metal nanoparticles coated with a thiol-polyethylene glycol;
  iii) purification of said composition obtained in step ii) by separating said nanoparticles from free thiol-polyethylene glycol and free CTAB;
  iv) adding a mercaptocarboxylic acid to said composition obtained in step iii), thereby obtaining a liquid composition comprising metal nanoparticles coated with a mercaptocarboxylic acid; and
  v) contacting said metal particles obtained in step iv) with said molecule.

In a further aspect, the present invention provides a method for conjugating a molecule to a nanoparticle, comprising:
  a) providing nanoparticles comprising one or more metals;
  b) providing said nanoparticles with one or more functional groups, or coupling the first molecule to a molecule comprising a metal binding functionality;
  c) conjugating said first molecule to said nanoparticles, whereby the amount of said first molecule attached to said nanoparticles is less than 70% of the amount required for full coverage of said nanoparticles with said first molecule;

The following examples are provided for the purpose of illustrating the present invention and by no means are meant and in no way should be interpreted to limit the scope of the present invention.

EXAMPLES

A) Preparation of Nanorods Coated by 11-Mercaptoundecanoic Acid a1) Preparation of CTAB-Coated Nanorods The method used for preparing the gold nanorods is similar to the method as described by Yu and Irudayaraj (*Anal. Chem.* 2007, 79, 572-579). In short, a seed solution was prepared by adding 0.5 mM hydrogen tetrachloroaurate (HAuCl$_4$) to 0.1M CTAB, after which 0.01M NaBH$_4$ solution is added.

Then, a growth solution was prepared by adding 42 mM AgNO$_3$ and then 1 mM HAuCl$_4$ to 0.1M CTAB solution. Immediately after preparing the growth solution, ascorbic acid solution is added to the growth solution. After change in color, seed solution is added, thereby generating CTAB-coated gold nanorods.

a2) Removal of Excess CTAB

After one week, excess CTAB was removed from the nanorod suspension by centrifuging the suspension at 10000 g for 30 minutes. Then, the supernatant (which contains most of the excess CTAB) was removed and the precipitated nanorods in the pellet were resuspended in (double-distilled) water.

a3) Exchange of CTAB to mPEG-SH

After removal of excess CTAB, the CTAB coating of the nanorods was exchanged to a sulfhydryl functionalized methoxy polyethylene glycol (mPEG-SH, available from Nanocs as "PEG3-0021") coating. First, a 10 g/L solution of mPEG-SH in (double-distilled) water was prepared. To this solution the same volume of purified nanorod suspension was added under stirring. Then, the mixture was sonicated for 5 minutes, followed by stirring for 12 hours at room temperature.

a4) Removal of Excess mPEG-SH

The suspension obtained in step a3) was centrifuged at 8000 g for 30 minutes at 25° C. After centrifugation, the supernatant was removed and the precipitated nanorods were resuspended in a (1× concentrate) tris/borate/EDTA (TBE) buffer. The centrifugation and resuspension cycle was repeated three times. After the last centrifugation step, the nanorods were resuspended in (1× concentrate) TBE buffer.

a5) Exchange of mPEG-SH Coating to MUDA

For the exchange of the mPEG-SH coating of the nanorods to a mercaptoundecanoic acid (MUDA) coating, a 60 g/L solution of MUDA in ethanol was prepared. This solution was added to the nanorod suspension obtained in step a4) resulting in a ca. 1.2 g/l MUDA concentration. Then, the suspension was sonicated for 5 minutes, followed by stirring for two hours. The suspension was then centrifuged at 5000 g for 30 minutes at 25° C., followed by removal of the supernatant and resuspension of the precipitated nanorods in 25 mL of TBE buffer. Then, 60 g/L MUDA solution in ethanol was added to the nanorod suspension (resulting in a final MUDA concentration of 1.2 g/l), followed by stirring for 12 hours.

a6) Removal of Excess MUDA

The nanorod suspension obtained in step a5) was centrifuged at 5000 g for 30 minutes at 25° C., followed by removal of the supernatant and resuspension of the precipitated nanorods in TBE buffer. The cycle of centrifuging and resuspension was repeated twice. After the last centrifugation step, the pellet was resuspended in 10 mM MES buffer comprising 0.002% (by volume) Tween (polysorbate). The suspension was then dialyzed against 10 mM MES buffer comprising 0.002% (by volume) Tween for one hour (3 L of buffer per 25 mL of nanorod suspension).

To obtain nanorods which are coated with a mixture of MUDA and another molecule, the method as described above can be used, with the difference that in step a5) a solution containing MUDA and that other molecule is used.

B) Conjugation of Nanorods with HAS

The amount of HSA necessary to obtain a full coverage of nanoparticles was determined by a concentration titration. A suspension comprising carboxylated (i.e. MUDA-coated) gold nanorods as described in example A) was provided. The carboxyl groups were activated using EDC and sulfo-NHS, and the nanorod suspension was mixed with increasing amounts of HSA in a range of 0 to 200 μg of protein per mL nanorod suspension.

Figure 1A:
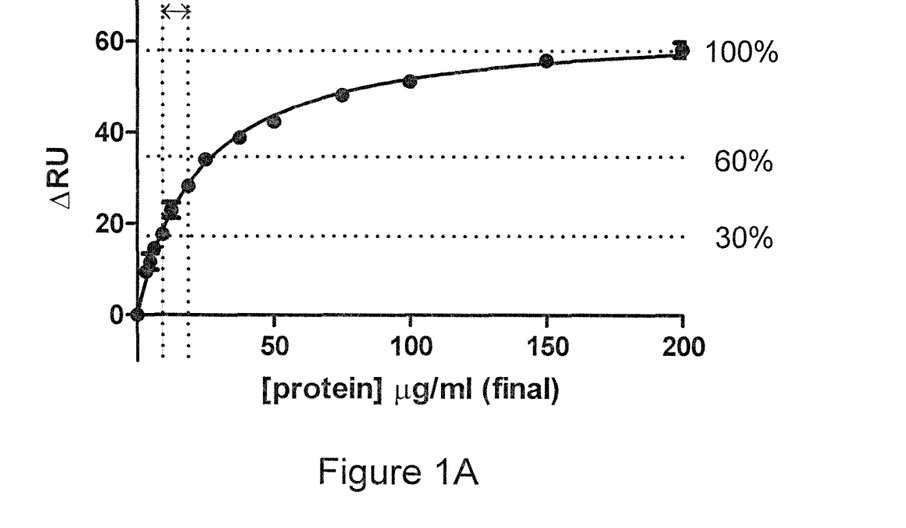
FIG. 1A demonstrates a protein titration curve for human Serum Albumin (HSA) and represents a plot of ΔRU (i.e. ΔOD($\lambda_{max}$+80)/OD($\lambda_{max}$)) against the amount of HSA per mL nanoparticle suspension.
Figure 1B:
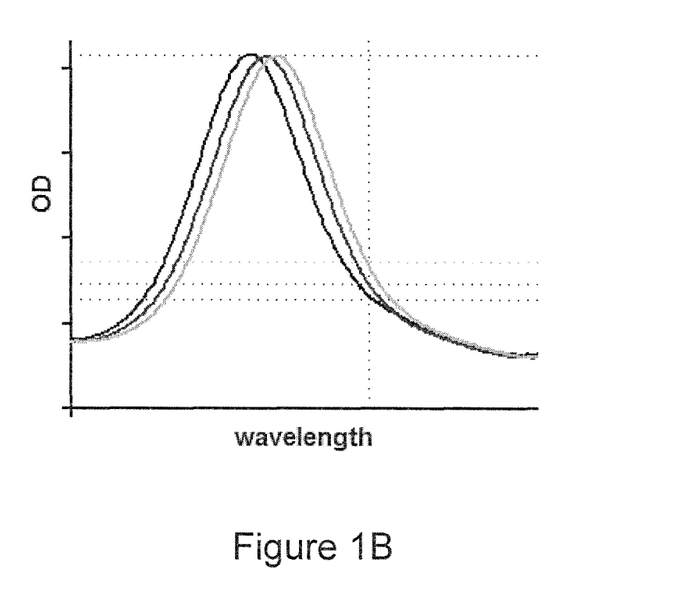
FIG. 1B shows the absorbance spectrum of identical nanorods, conjugated with different amounts of a protein.

Absorbance spectra of these samples were recorded and ΔRU, which is the change in the ratio $(OD(\lambda_{max}+80))/(OD\lambda_{max})$, i.e. the ratio of the optical density at $\lambda_{max}+80$ nm $(OD(\lambda_{max}+80))$ and the optical density at the peak value $(OD\lambda_{max})$ was plotted against the amount of HSA per mL of nanoparticle suspension. The ratio of these optical densities provides information about the amount of conjugated HSA. A plot of ΔRU vs. the HSA amount is shown in FIG. 1A, which shows that increased amounts of added HSA result in an increased change of ΔRU, which can be understood as an increased amount of conjugated HSA surrounding the particles. Indeed, the attachment of protein to the nanomaterial leads to a difference in refractive index around the nanomaterial and thereby to a redshift of the $\lambda_{max}$ that can be detected by reading an absorbance spectrum. The effect of protein conjugation on the optical density (OD) of a gold nanorod suspension is shown in FIG. 1B. Higher amounts of conjugated protein lead to increasing redshifts of the spectrum i.e. shifts to higher wavelengths.

FIG. 1A shows that after reaching the maximum amount (100%) of protein that can be attached to the nanomaterial, the spectrum does not change anymore resulting in a plateau in the plot of ΔRU versus the amount of protein.

The lowest amount of protein on the plateau is the minimum amount of protein needed to fully cover the nanomaterial with the protein of interest.

In a particular embodiment of the present invention, the optimal amount of protein to use is the amount that corresponds to 30-60% of the plateau. In the present example this corresponds to 9-25 μg/mL protein, as shown in FIG. 1.

In this range, a sufficiently low amount of protein is attached to the rods to avoid ligand depletion, and a sufficiently high amount of protein is attached for providing a significant redshift of $\lambda_{max}$ upon binding of a binding partner.

C) Effect of Binding Site Density on $K_d$ Determination

To study the effect of the amount of binding sites provided on the nanoparticles on the measured binding properties such as the dissociation constant ($K_d$), a carboxylated nanorod suspension as used in example B) was divided in two groups. The two groups were conjugated with HSA by activation of the carboxyl groups with EDC/sulfo-NHS and mixing the suspension with 600 μg/mL HSA (sample 1) and 18.75 μg/mL HSA (sample 2), respectively. The unreacted carboxyl groups present on the nanorod surface were blocked by addition of BSA. In accordance with the results of Example A), full coverage of the nanorods with HSA was obtained in sample 1, while only a partial coverage was obtained in sample 2.

The two solutions were contacted with Anti-Human Serum Albumin monoclonal antibody (ab18081, available from Abcam®) in identical conditions. After an incubation time of 30 minutes, absorption spectra of the suspensions were recorded.

Figure 2:
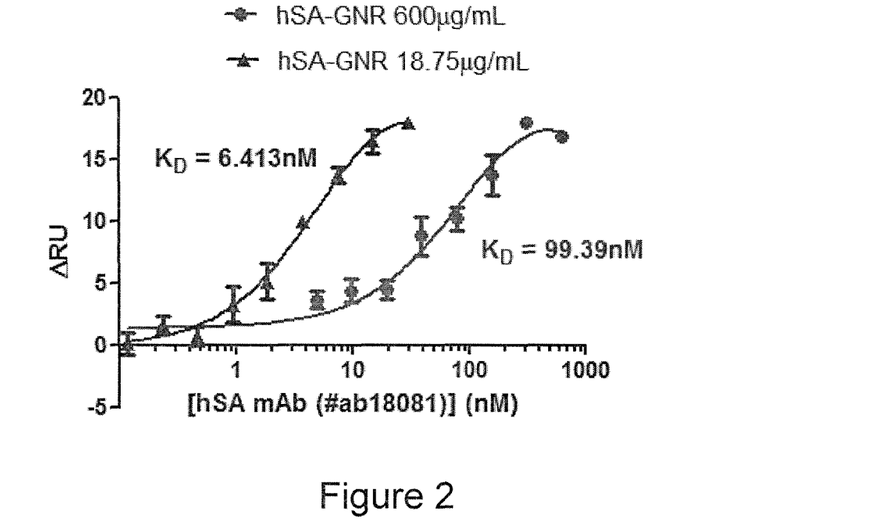
FIG. 2 represents a plot of ΔRU against the amount of antibody per mL nanoparticle-HSA conjugate suspension.

FIG. 2 shows the effect of addition of various amounts of the antibody to the optical properties of the two suspensions at equilibrium. In all cases, increased antibody addition results in an increased change of in the ratio of OD($\lambda_{max}$+80))/OD$\lambda_{max}$, indicative of increased amounts of HSA molecules binding with the antibody.

From the absorbance data, dose response curves could be constructed, from which the dissociation constant $K_d$ for the HSA-antibody association-dissociation equilibrium was calculated. The results are given in Table 1. With full coverage (sample 1), the $K_d$ calculated from the experiments strongly deviate from the correct value as determined for sample 2. This deviation can be attributed to ligand depletion.

TABLE 1

Results of $K_d$ determination with different binding site density

| Sample | [HSA] (μg/mL) | $K_d$ (nM) |
|---|---|---|
| 1 | 600 | 99.39 |
| 2 | 18.75 | 6.413 |

Similar results are obtained when using other blocking agents. Table 2 shows Kd values obtained using methoxy-PEG-amine (mPEG-NH$_2$), BSA and ovalbumine. The incubation time was 60 minutes for each blocking agent. The results shown in Table 2 indicate that the obtained values for $K_d$ are equal within the margin of error.

TABLE 2

Results of $K_d$ determination with different blocking agents

| Blocking agent | Amount of blocking agent used (μg/mL) | $K_d$ (nM) |
|---|---|---|
| mPEG-NH$_2$ | 16700 | 2.5 ± 1.6 |
| BSA | 200 | 8.44 ± 5.7 |
| Ovalbumine | 200 | 5.22 ± 3.3 |

A similar batch of gold nanorods was divided in three groups. The groups were conjugated with HSA by mixing the suspension with 600 μg/mL HSA (sample 1), 37.5 μg/mL HSA (sample 2) and 18.75 μg/mL HSA (sample 3), respectively. The unreacted carboxyl groups present on the nanorod surface were blocked by addition of BSA. In accordance with the results of Example B), full coverage of the nanorods was obtained in sample 1, while only a partial coverage was obtained in sample 2 and 3.

The three solutions were contacted with Anti-Human Serum Albumin monoclonal antibody (ab18081, available from Abcam®) in identical conditions. After an incubation time of 60 minutes, absorption spectra of the suspensions were recorded, from which the dissociation constant $K_d$ for the HSA-antibody association-dissociation equilibrium was calculated. The results are given in Table 3. With full coverage (sample 1), the $K_d$ calculated from the experiments again strongly deviate from the correct value as determined for sample 2 and 3. Again, this deviation can be attributed to ligand depletion.

TABLE 3

Results of $K_d$ determination with different binding site density

| Sample | [HSA] (μg/mL) | $K_d$ (nM) |
|---|---|---|
| 1 | 600 | 252.4 ± 47.1 |
| 2 | 37.5 | 5.5 ± 1.25 |
| 3 | 18.75 | 3.8 ± 1 |

D) MUDA-Functionalization of a Protein and mPEG-SH Exchange

The first molecule of interest in this example is BSA. BSA was covalently modified on its primary amine with a thiol-linker, more particularly MUDA. For this reaction, the carboxyl moiety of MUDA was activated with EDC and sulfo-NHS.

An excess of the modified BSA (BSA_MUDA) was then added to a suspension of purified mPEG-SH coated nanorods, as obtained in step a4) of example A) described above. This results in a (partial) exchange of mPEG-SH by BSA_MUDA at the nanorod surface. The exchange is slow and takes a few hours to several days.

Figure 3:
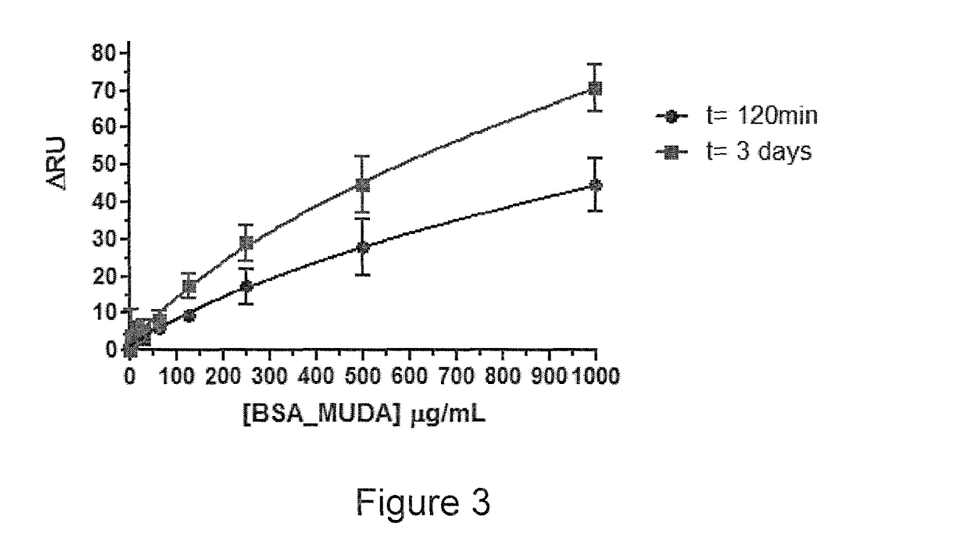
FIG. 3 represents a plot of ΔRU against the amount of BSA_MUDA added to a suspension of mPEG-SH coated gold nanorods.

FIG. 3 shows a concentration titration of mPEG-SH coated nanorods with BSA_MUDA. Addition of larger amounts of BSA_MUDA typically leads to an increased exchange of mPEG-SH by BSA_MUDA, indicated by an increased ΔRU. From measurement of the same samples after 120 minutes and 3 days, it is clear that longer exchange times lead to increased exchange.

E) Conjugation Via Click Chemistry or Staudinger Ligation e1) Click Chemistry

Figure 4:
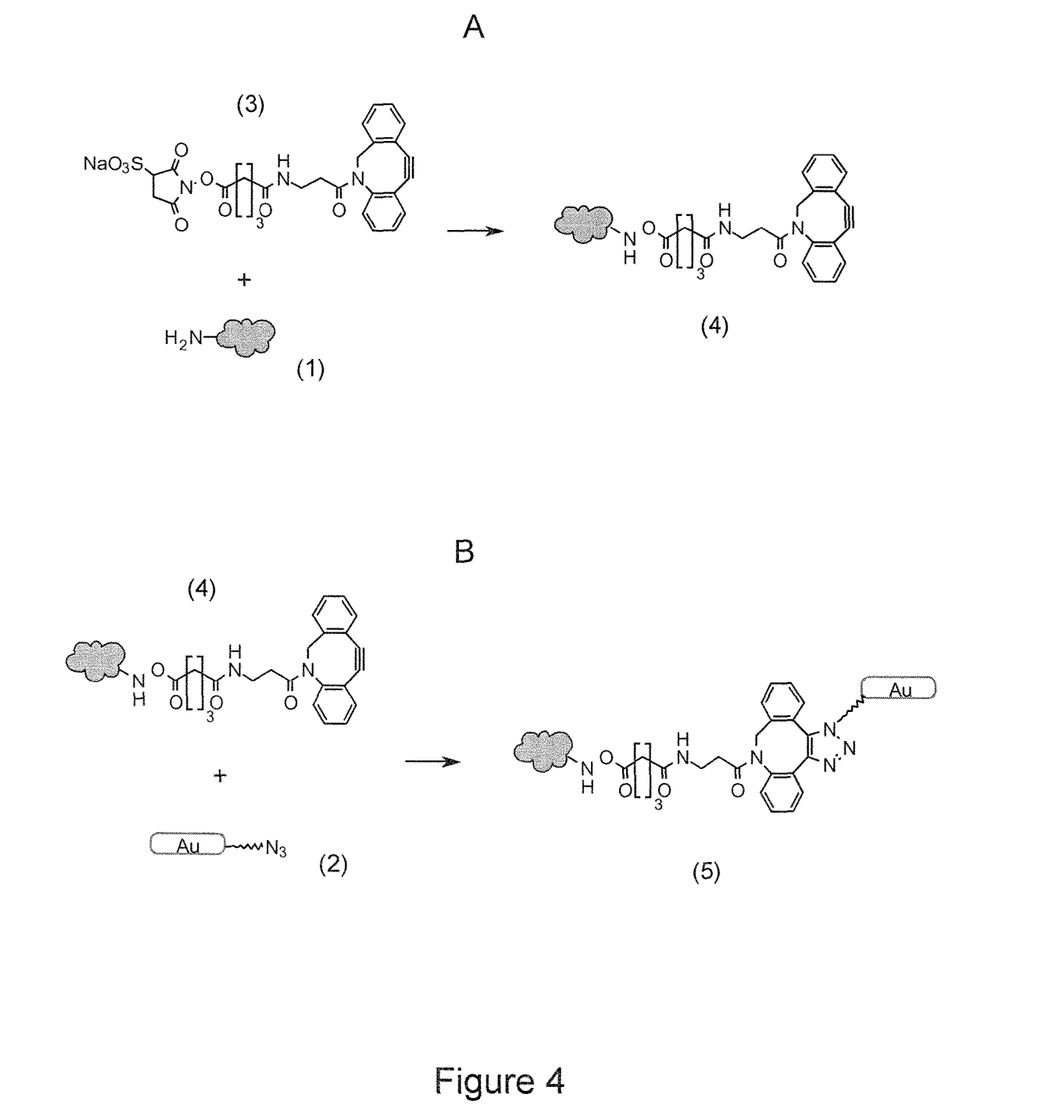
FIG. 4 shows a conjugation between a first molecule (1) and a nanoparticle (2) according to a particular embodiment of the present invention.

FIG. 4 shows a conjugation between a first molecule (1) and a nanoparticle (2) according to a particular embodiment of the present invention. The first molecule (1) is a protein and the nanoparticle (2) is a gold nanorod provided with azide functional groups. In a first step (A), the protein (1) is provided with an alkyne moiety by reacting an amino moiety of the protein with the succinimidyl moiety of compound (3). In a second step (B), the functionalized protein (4) is conjugated to the nanoparticle (2) via an azide alkyne Huisgen cycloaddition reaction, thereby providing a nanoparticle conjugate (5).

e2) Staudinger Ligation

Figure 5:
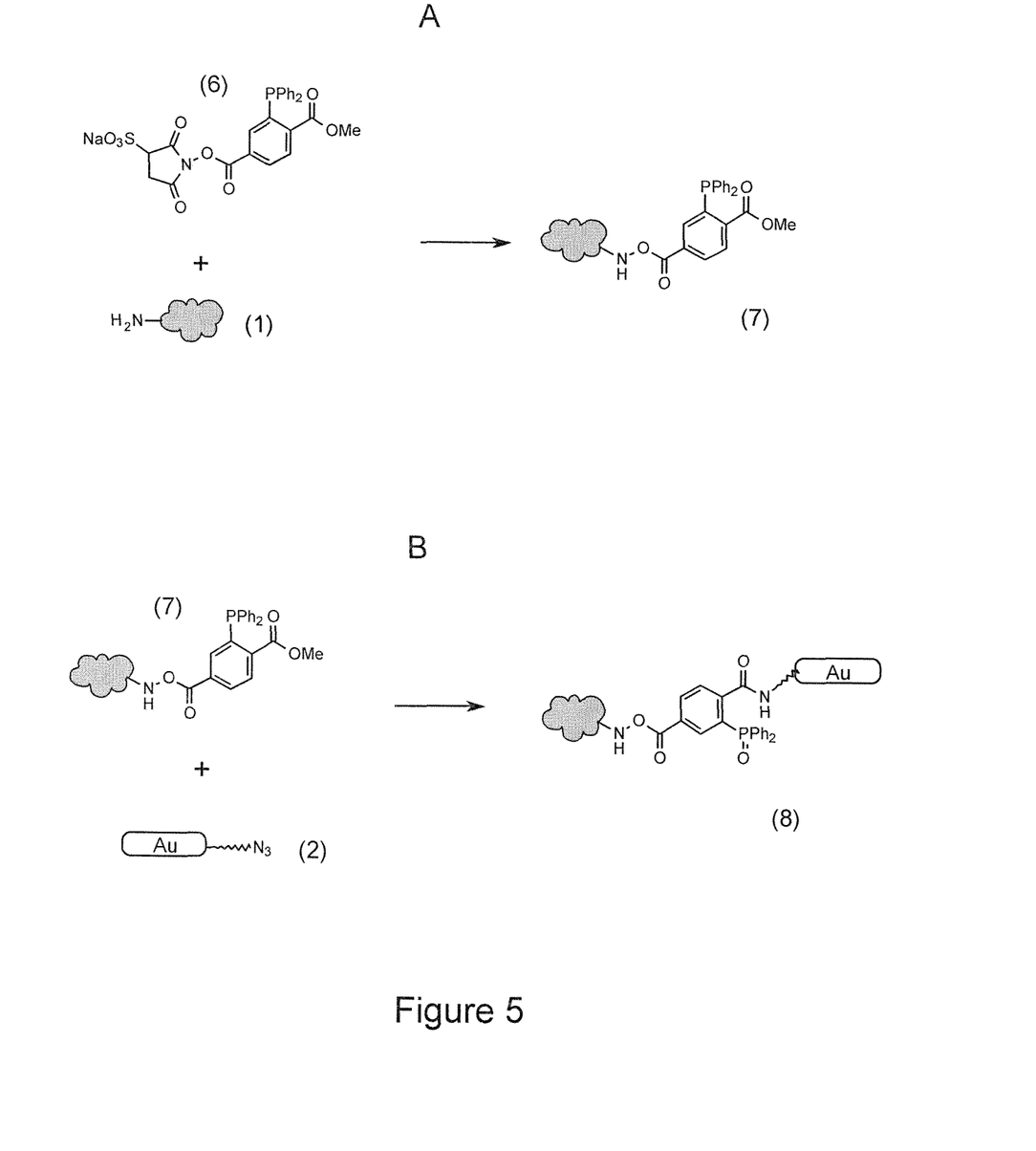
FIG. 5 shows a conjugation between a first molecule (1) and a nanoparticle (2) according to a particular embodiment of the present invention.

FIG. 5 shows a conjugation between a first molecule (1) and a nanoparticle (2) according to a particular embodiment of the present invention. The first molecule (1) is a protein and the nanoparticle (2) is a gold nanorod provided with azide functional groups. In a first step (A), the protein (1) is provided with a triarylphosphine moiety (comprising an ester group situated ortho to the phosphorus) by reacting an amino moiety of the protein with the succinimidyl moiety of compound (6). In a second step (B), the functionalized protein (7) is conjugated to the nanoparticle (2) via a Staudinger reaction, thereby providing a nanoparticle conjugate (8).

What is claimed is:

1. A method of determining an interaction between a first and a second molecule comprising:
    a) providing nanorods comprising one or more metals and having an aspect ratio between 1.5 and 5;
    b) providing said nanorods with one or more functional groups, or coupling said first molecule to a molecule comprising a metal binding functionality;
    c) conjugating said first molecule to said nanorods, wherein the amount of said first molecule attached to said nanorods is between 30% and 70% of the minimum amount required for full coverage of said nanorods with said first molecule;
    d) incubating said nanorods with said second molecule;
    e) monitoring step d) by illuminating said nanorods with at least one excitation light source and monitoring one or more optical properties of said nanorods; and
    f) detecting a change of one or more optical properties of said nanorods wherein said change is a result of the presence of a binding an interaction between said first molecule and said second molecule.

2. The method according to claim 1, wherein said nanorods comprise gold, silver or copper.

3. The method according to claim 1, wherein step f) comprises determining the equilibrium dissociation constant of the binding or interaction between said first and second molecule.

4. The method according to claim 1, wherein step f) comprises measuring said one or more optical properties at two or more wavelengths ranging between 350 and 1000 nm.

5. The method according to claim 4, wherein step f) comprises measuring the absorbance of said nanorods at two or more wavelengths ranging between 350 and 1000 nm.

6. The method according to claim 1, wherein step b) comprises providing nanorods having attached to their surface:
    one or more molecules comprising a metal binding functionality, and a functional group selected from carboxyl, amino, azido, alkynyl, carbonyl and hydroxyl; and
    one or more molecules comprising said metal binding functionality and not comprising said functional group selected from carboxyl, amino, azido, alkynyl, carbonyl and hydroxyl.

7. The method according to claim 1, wherein step c) comprises:
    c1) optionally, selecting a suitable pH and ionic strength for conjugation of said first molecule with said nanorods via a buffer test;
    c2) determining the amount of said first molecule needed for conjugation of said first molecule to said nanorods;
    c3) conjugation of said first molecule to said nanorods, based on the information obtained in step c2) and optionally c1).

8. The method according to claim 7, wherein step c2) comprises a concentration titration of said nanorods with said first molecule, optionally at the pH and ionic strength selected in step c1), for determining the minimal amount of said first molecule required for full coverage of said nanorods with said first molecule.

9. The method according to claim 1, wherein said step b) comprises coupling said first molecule to a linker molecule having a metal binding functionality and step c) comprises by conjugation of said first molecule to said nanorod via said linker molecule.

10. The method according to claim 9, wherein said linker molecule is a mercaptocarboxylic acid.

11. The method according to claim 1, wherein said first molecule is a protein and the surface of said nanorods is provided with carboxyl groups.

12. The method according to claim 11, further comprising reacting free carboxyl groups on the surface of said nanorods with a carboxyl blocking compound.

13. The method according to claim 1, wherein the amount of said first molecule attached to said nanorods is between 30% and 50% of the minimum amount required for full coverage of said nanorods with said first molecule.

* * * * *